United States Patent [19]

Olson et al.

[11] 4,159,282

[45] Jun. 26, 1979

[54] XYLENE ISOMERIZATION

[75] Inventors: David H. Olson, Pennington; Werner O. Haag, Trenton, both of N.J.

[73] Assignee: Mobil Oil Corporation, New York, N.Y.

[21] Appl. No.: 913,999

[22] Filed: Jun. 9, 1978

[51] Int. Cl.$^2$ ............................................. C07C 5/24
[52] U.S. Cl. .................................................. 585/481
[58] Field of Search ..................................... 260/668 A

[56] References Cited

U.S. PATENT DOCUMENTS

| 3,856,871 | 12/1974 | Haag et al. | 260/668 A |
| 3,856,872 | 12/1974 | Morrison | 260/668 A |

Primary Examiner—Veronica O'Keefe

Attorney, Agent, or Firm—Charles A. Huggett; Raymond W. Barclay

[57] ABSTRACT

A catalytic process is provided for isomerizing an isomerization feed containing an aromatic $C_8$ mixture of ethylbenzene and xylene in which the para-xylene content is less than equilibrium which comprises contacting said feed, under conversion conditions, with a catalyst comprising a crystalline aluminosilicate zeolite having a crystal size of at least about 1 micron, a silica to alumina ratio of at least about 12 and a constraint index, as hereinafter defined, within the approximate range of 1 to 12 to yield an isomerization product characterized by a reduced ethylbenzene content and an enhanced paraxylene content.

13 Claims, 5 Drawing Figures

XYLENE ISOMERIZATION

BACKGROUND OF THE INVENTION

1. Field of the Invention

This invention relates to a process for effecting isomerization of an aromatic $C_8$ mixture comprising ethylbenzene and xylene in the presence of a specified crystalline aluminosilicate zeolite catalyst characterized by a crystal size of at least about 1 micron.

2. Description of the Prior Art

Xylenes are valuable industrial chemicals. They are derived primarily from such aromatic naphthas as petroleum reformates and pyrolysis gasolines. The former result from processing petroleum naphthas over a catalyst such as platinum on alumina at temperatures which favor dehydrogenation of naphthenes. Pyrolysis gasolines are liquid products resulting from steam cracking of hydrocarbons to manufacture ethylene, propylene, etc.

Generally and regardless of aromatic naphtha source, it has been the practice to subject the liquid hydrocarbon to extraction with a solvent highly selective for aromatics to obtain an aromatic mixture of the benzene and alkylated benzenes present in the aromatic naphtha. The resulting aromatic extract may then be distilled to separate benzene, toluene and $C_8$ aromatics from higher boiling compounds in the extract. Benzene and toluene are recovered in high purity but the $C_8$ fraction, containing valuable para xylene, is a mixture of the three xylene isomers with ethylbenzene. Techniques are known for separating p-xylene by fractional crystallization with isomerization of the other two isomers in a loop to the p-xylene separation. That operation is hampered by the presence of ethylbenzene. However, a widely used xylene isomerization technique, "Octafining" can be applied. Octafining by passing the $C_8$ aromatics lean in p-xylene and mixed with hydrogen over platinum on silica-alumina not only isomerizes xylenes but also converts ethylbenzene, thus preventing buildup of this compound in the separation-isomerization loop.

The manner of producing p-xylene by a loop including Octafining can be understood by consideration of a typical charge from reforming petroleum naphtha. The $C_8$ aromatics in such mixtures and their properties are:

| | Freezing Point °F. | Boiling Point °F. | Density Lbs./U.S. Gal. |
|---|---|---|---|
| Ethylbenzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Individual isomer products may be separated from the naturally occuring mixtures by appropriate physical methods. Ethylbenzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes. Of the xylene isomers, i.e., ortho-, meta and para-xylene, meta-xylene is the least desired product with ortho- and para-xylene being the more desired products. Para-xylene is of particular value being useful in the manufacture of terephthalic acid which is an intermediate in the manufacture of synthetic fibers such as "Dacron".

Isomerization processes operate in conjunction with the product xylene of xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

A typical charge to the isomerizing reactor may contain 17 wt. % ethylbenzene, 65 wt. % m-xylene, 11 wt. % p-xylene and 7 wt. % o-xylene when it is desired to co-produce orthoxylene and para-xylene. When para-xylene is desired as the sole product, a typical charge may contain 20 wt. % ethylbenzene, 51 wt. % m-xylene, 9 wt. % para-xylene and 20 wt. % orthoxylene. The thermodynamic equilibrium varies slightly with temperature. The objective in the isomerization reactor is to bring the charge as near to the equilibrium concentration as may be feasible consistent with reaction times which do not give extensive cracking and disproportionation.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethane and benzene and hydrocracking of the alkyl cyclohexanes.

The rate of ethylbenzene approach to equilibrium concentration in a $C_8$ aromatic mixture is related to effective contact time. Hydrogen partial pressure has a very significant effect on ethylbenzene approach to equilibrium. Temperature change within the range of Octafining conditions (830° to 900° F.) has but a very small effect on ethylbenzene approach to equilibrium.

Concurrent loss of ethylbenzene to other molecular weight products relate to % approach to equilibrium. Products formed from ethylbenzene include $C_8^+$ naphthenes, benzene from cracking benzene and $C_{10}$ aromatics from disproportionation, and total loss to other than $C_8$ molecular weight. $C_5$ and lighter hydrocarbon by-products are also formed.

The three xylenes isomerize much more selectively than does ethylbenzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethylbenzene has been found responsible for a relatively rapid decline in catalyst activity and this effect is proportional to its concentration in a $C_8$ aromatic feed mixture. It has been possible then to relate catalyst stability (or loss in activity) to feed composition (ethylbenzene content and hydrogen recycle ratio) so that for any $C_8$ aromatic feed, desired xylene products can be made with a selected suitably long catalyst use cycle.

Because of its behavior in the loop manufacture of p-xylene, or other xylene isomer, ethylbenzene is undesirable in the feed but is tolerated because of the great expense of removal from mixed $C_8$ aromatics. Streams substantially free of ethylbenzene are available from such processes as transalkylation of aromatics having only methyl substituents. Thus, toluene can be reacted with itself (the specific transalkylation reaction sometimes called "disproportionation") or toluene may be reacted with tri-methyl benzene in known manner.

A recent development in vapor phase isomerization is described in U.S. Pat. No. 3,856,872 (Morrison) dated Dec. 24, 1974. It is there shown that use of a catalyst containing HZSM-5 is very efficient for isomerization of xylenes at reduced hydrogen flow as compared with Octafining. The extent of xylene loss is substantially reduced by this change of catalyst. Concurrently, the mechanism of ethylbenzene conversion is drastically changed on substitution of, e.g., NiHZSM-5, for the platinum on silica/alumina of Octafiners. The Morrison process results in conversion of ethylbenzene by transalkylation reactions including disproportionation of ethylbenzene to benzene and diethylbenzene, disproportionation and ethylation of xylene and the like producing alkyl aromatic compounds of nine or more carbon atoms ($C_9+$) together with benzene and toluene. Those conversion products are readily separated in the loop for recovery of p-xylene and isomerization of o- and m-xylenes. In general, loss of xylenes increases as severity of the isomerizer is increased to enhance the conversion of ethylbenzene. Xylene isomerization may also be carried out in the liquid phase, using a similar crystalline aluminosilicate zeolite catalyst, as described in U.S. Pat. No. 3,856,871.

SUMMARY OF THE INVENTION

In accordance with the present invention, there has been discovered a process for effecting isomerization of a feed containing an aromatic $C_8$ mixture of ethylbenzene and xylene in which the para-xylene content is less than equilibrium to yield a product of reduced ethylbenzene content and enhanced para-xylene content by contact of such mixture, at elevated temperatures, with a catalyst comprising a crystalline aluminosilicate zeolite having a crystal size of at least about 1 micron, usually in the approximate range of 1 to 20 microns and preferably 1 to 6 microns. The crystalline aluminosilicate zeolite is essentially characterized by a silica to alumina ratio of at least about 12 and a constraint index within the approximate range of 1 to 12. In one embodiment, the crystalline aluminosilicate zeolites employed have a xylene sorption capacity greater than 1 gram/100 grams of zeolite and an ortho-xylene sorption time for 30 percent of said capacity of greater than 10 minutes, where the sorption capacity and sorption times are measured at 120° C. and a xylene pressure of 4.5±0.8 mm. of mercury.

The present process comprises isomerization of an aromatic $C_8$ mixture in the presence of the specified catalyst at a temperature between about 400 and about 1000° F. at a pressure between about atmospheric and about 1500 psig utilizing a feed weight hourly space velocity (WHSV) between about 0.5 and about 100. The latter WHSV is based on the weight of catalyst composition, i.e., total weight of active catalyst and binder therefor. Preferably, but not necessarily the desired isomerization is effected in the presence of hydrogen. Hydrogen may be present in the isomerization zone in an amount between about 0 and about 10 and preferably between about 1 and about 5 moles of hydrogen per mole of hydrocarbon. The above process conditions include operation in liquid, vapor or mixed phase.

DESCRIPTION OF SPECIFIC EMBODIMENTS

Figure 1:
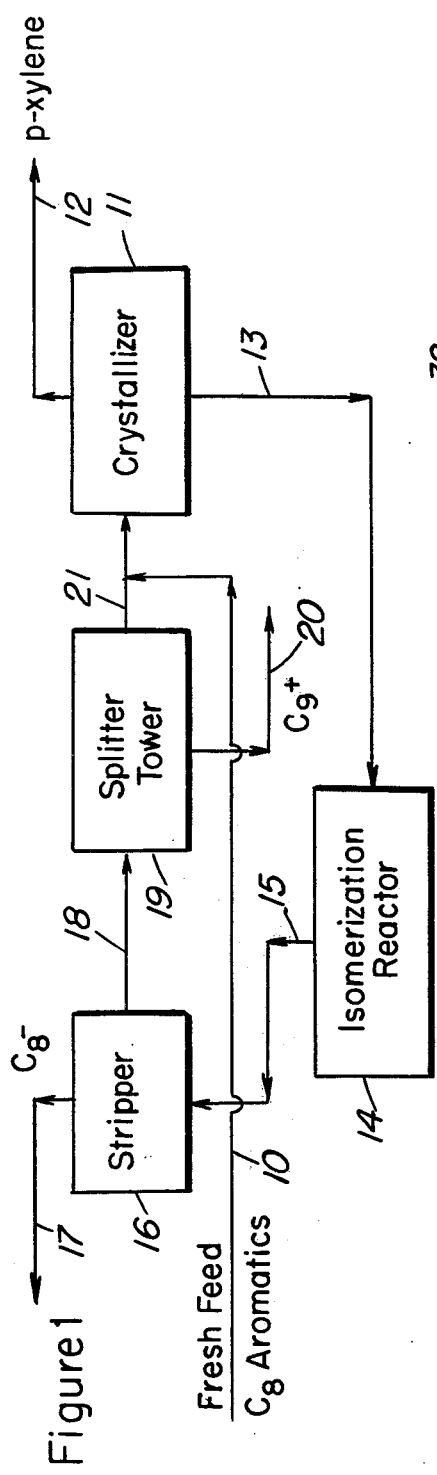
FIG. 1 shows, in schematic fashion, a system utilizing a single isomerization reactor containing crystalline zeolite catalysts of differing crystallite size.

It is contemplated that any aromatic $C_8$ mixture containing ethylbenzene and xylene may be used as feed to the process of this invention. Generally, such mixture will have an ethylbenzene content in the approximate range of 5 to 50 weight percent, an ortho xylene content in the approximate range of 0 to 35 weight percent, a meta xylene content in the approximate range of 20 to 95 weight percent and a para xylene content in the approximate range of 0 to 15 weight percent. The feed in addition to the above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from platinum reforming of a petroleum naphtha to a mixture of reduced ethylbenzene content and increased content of para-xylene.

In accordance with the present invention, such feed is brought into contact, under conversion conditions, with a catalyst comprising a crystalline aluminosilicate zeolite having a crystal size of at least about 1 micron, a silica to alumina ratio of at least about 12 and a constraint index within the approximate range of 1 to 12.

The zeolites herein described are members of a novel class of zeolites exhibiting some unusual properties. These zeolites induce profound transformation of aliphatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the crystalline free space.

The silica to alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions although puckered structures exist such as TMA Offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 100° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite has been found to be an important factor affecting the desired isomerization of $C_8$ aromatic mixtures. The crystal size of the above-described crystalline aluminosilicate zeolite employed in the process of the invention is at least about 1 micron, being in the approximate range of 1-20 microns and particularly in the range of 1-6 microns. With the use of crystals within such size range, distinctly higher selectivity of production of the desired para-xylene has been observed as compared with comparable use of smaller size crystals.

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

In practicing the desired isomerization process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families includes the sub-bentonites and the kaolins commonly known as Dixie, McNamee:Georgia and Florida clays or others in which the main mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

In the process of the invention, the feed consisting essentially of a mixture of $C_8$ aromatic hydrocarbons including ethylbenzene and xylene is contacted with the above-described catalyst bed at a temperature of about 400° F. to about 1000° F. and preferably between about 500° F. to about 950° F., a contact time equivalent to or the same as a weight hourly space velocity (WHSV) of about 0.5 to about 100 and preferably about 1 to about 50, it being understood that WHSV signifies pounds of feed per pound of zeolite per hour and at a pressure of about 0 to about 1500 psig, preferably between about 25 and about 1000 psig. Hydrogen may be co-fed along with the feed to retard catalyst aging, utilizing a hydrogen/feed mole ratio between about 0 and about 10.

In one embodiment, the crystalline aluminosilicate zeolites employed are modified prior to use to exhibit a xylene sorption capacity greater than 1 gram/100 grams of zeolite and an ortho zylene sorption time for 30 percent of said capacity of greater than 10 minutes, said sorption capacity and sorption time being measured at 120° C. and a xylene pressure of 4.5±0.8 mm. of mercury. This may be accomplished by combining with the crystalline aluminosilicate zeolite a small amount, generally in the range of about 0.5 to about 40 weight percent, preferably of a difficulty reducible oxide, such as the oxides of phosphorus, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5±0.8 mm. of mercury and an ortho-xylene sorption time for 30 percent of said capacity of greater than 10 minutes (at the same conditions of temperature and pressure) are required in order to achieve the desired selective production of para-xylene.

It has been found that zeolites exhibiting very high selectivity for para-xylene production require a very long time up to and exceeding a thousand minutes to sorb o-xylene in an amount of 30% of total xylene sorption capacity. For those materials, it is more convenient to determine the sorption time for a lower extent of sorption, such as 5%, 10% or 20% of capacity, and to estimate the 30% sorption time by applying the following multiplication factors F as illustrated for 5% sorption:

$t_{0.3} = F \cdot t_{0.05}$

| Percent of sorption capacity | Factor (F) to Estimate 30% Sorption Time |
| --- | --- |
| 5 | 36 |
| 10 | 9 |
| 20 | 2.2 |

Representative phosphorus-containing compounds which may be used include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphate. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P)S)Cl$ and $R_2P(S)Cl$.

Preferred phosphorus-containing compounds include diphenyl phosphine chloride, trimethylphosphite and phosphorus trichloride, phosphoric acid, ammonium hydrogen phosphites, including dihydrogen ammonium phosphate and diammonium hydrogen phosphite, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Reaction of the zeolite with the phosphorous compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures. i.e., up to about 500° C. are preferred. Heating is generally carried out for 3-5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.5 percent by weight. However, it is preferred that the amount of phosphorus in the zeolite be at least about 2 percent by weight when the same is combined with a binder, e.g., 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium proprionate, magnesium 2-ethylhexoate, magnesium carbonate, magnesium formate, magnesium oxalate, magnesium amide, magnesium bromide, magnesium hydride, magnesium lactate, magnesium laurate, magnesium oleate, magnesium plamitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e., may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, i.e. up to about 500° C. are preferred. Heating is generally carried out for 1-5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g., 35 weight percent of alumina. The amount of magnesium oxide can be as high as about 25 percent by weight or more depending on the amount and type of binder present. Preferably, the amount of magnesium oxide added to the zeolite is between about 1 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron-containing compound is, for example, trimethylborate, a hydrocarbon solvent such as n-octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite such as nitrogen or helium or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of boron incorporated with the zeolite should be at least about 0.2 percent by weight. However, it is preferred that the amount of boron in the zeolite be at least about 1 percent by weight when the same is combined with a binder, e.g., 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally, the amount of $Sb_2O_3$ in the composite catalyst will be between about 6 and about 40 weight percent and preferably between about 10 and about 35 weight percent. Antimony derivatives which may be used include: the hydrides $SbH_3$; the halides $MX_3$, $MX_5$ (M=Sb, X=F, Cl, Br, I); organic alkyl and aryl stibines and their oxides $R_3Sb$, $R_5Sb$, $R_xSb=O$ (R-alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO$. OH, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; and antimonyl salts as $(SbO)SO_4$, $(SbO)NO_3$, $K(SbO)C_4H_4O_6$, $NaSbO_2 \cdot 3H_2O$.

In some instances, it may be desirable to modify the crystalline aluminosilicate zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 0.5 and about 40 weight percent.

Still another modifying treatment entails steaming of the zeolite by contact with an atmosphere containing from about 5 to about 100 percent steam at a temperature of from about 250° to about 800° C. for a period of between about 0.25 and about 100 hours and under pressures ranging from sub-atmospheric to several hundred atmospheres to reduce the alpha value thereof determined at 1000° F., following the general procedure described in the Journal of Catalysis, Volume VI, pages 278–287, 1966, to less than 500 and preferably less than 100 but greater than zero.

Another modifying treatment involves precoking of the catalyst to deposit a coating of between about 1 and about 50 and preferably between about 2 and about 20 weight percent of coke thereon. Precoking can be accomplished by contacting the catalyst with a hydrocarbon charge, e.g., toluene, or preferably the hydrocarbon feed employed in the process, under high severity conditions or alternatively at a reduced hydrogen to hydrocarbon concentration, i.e., 0 to 1 mole ratio of hydrogen to hydrocarbon for a sufficient time to deposit the desired amount of coke thereon.

It is also contemplated that a combination of steaming and precoking of the catalyst under the above conditions may be employed to suitably modify the crystalline aluminosilicate zeolite catalyst.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g., air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used initially to burn the coke in a controlled manner so as to limit the temperature to a maximum of around 500°–550° C.

In general, the xylene isomerization reaction is carried out in a fixed bed flow reactor containing the specified crystalline aluminosilicate catalyst in which the majority of the crystals are greater than about 1 micron, as determined by electron microscope examination. In more specific embodiments, the reaction is carried out with the crystalline aluminosilicate catalyst having a bimodal crystal size distribution generally falling in the two ranges, less than about 1 micron and greater than about 1 micron, with the latter being in major proportion.

In one embodiment, as illustrated in FIG. 1, the catalyst may be in a single reactor where either the crystalline aluminosilicate zeolite catalysts of differing crystal size are in sequential beds, with the catalyst crystals of greater than about 1 micron size preceding the catalyst crystals of less than about 1 micron size or the differing crystal size catalysts may be present as a physical mixture.

Figure 2:
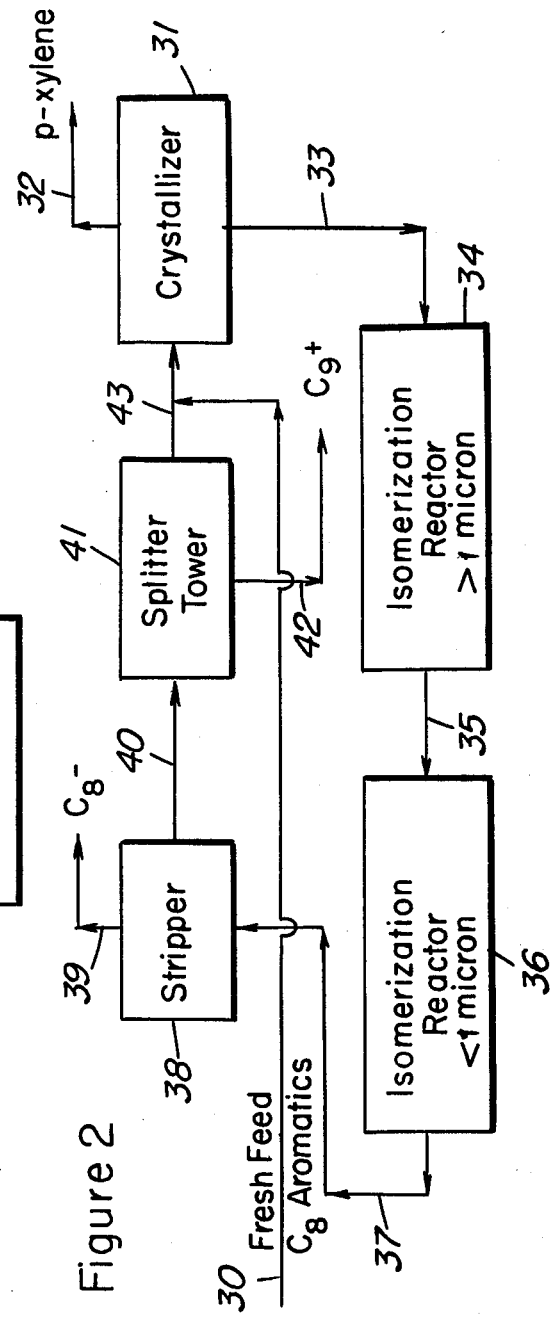
FIG. 2 shows, in schematic fashion, a system utilizing a dual isomerization reactor sequence individually containing crystalline aluminosilicate zeolite catalysts of differing crystallite size.

In another embodiment, as shown in FIG. 2, the catalysts of differing crystal size may be in separate reactors maintained at the same temperature or at different temperatures with the temperature in the first reactor being higher than in the second and with the reactor containing the catalyst crystals of greater than about 1 micron preceding the reactor containing the catalyst crystals of less than 1 micron size.

Figure 3:
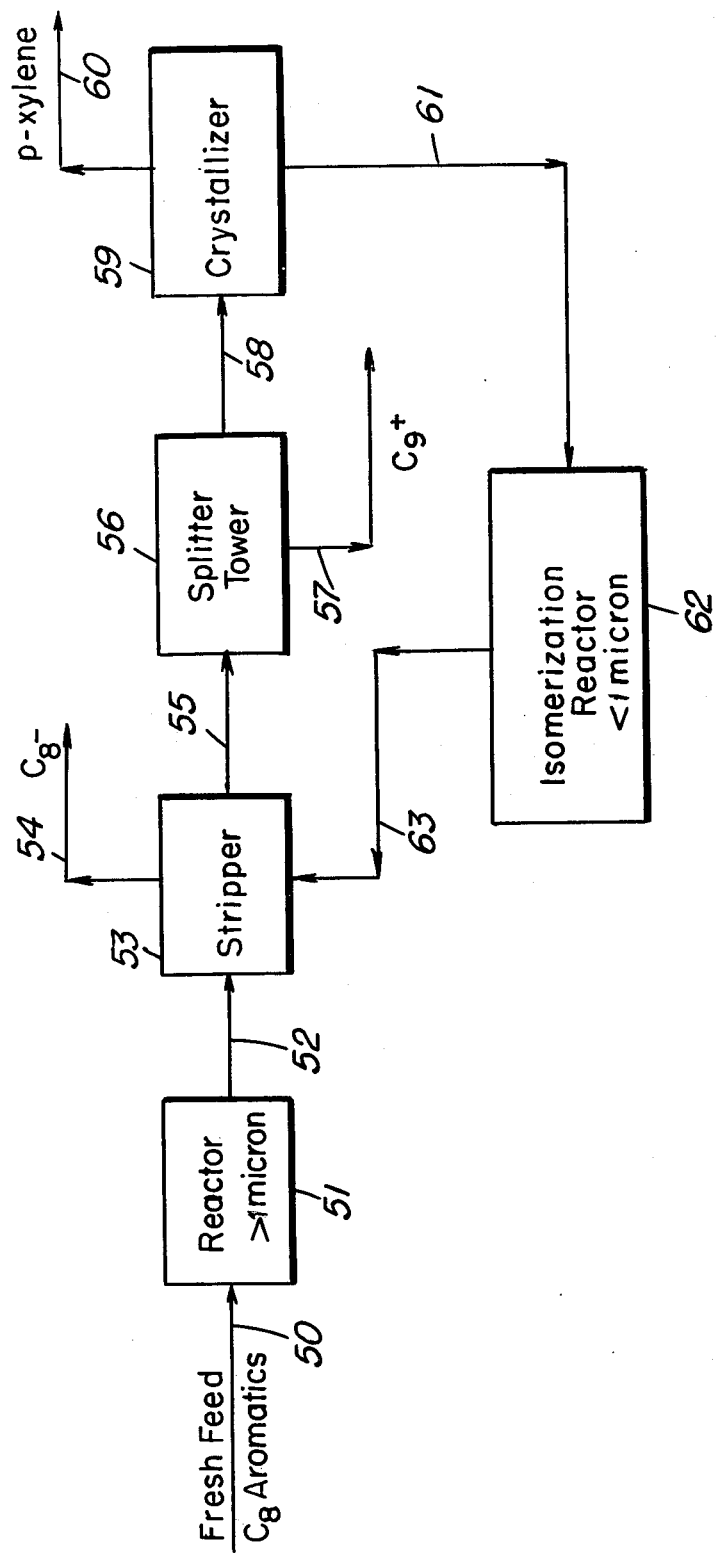
FIG. 3 shows, in schematic fashion, a system utilizing an initial isomerization reactor and a second reactor contained in the recycle loop using crystalline aluminosilicate zeolite catalysts of differing crystallite size.

In still another embodiment, illustrated in FIG. 3, the crystalline aluminosilicate zeolite catalyst of greater than about 1 micron size is contained in a separate reactor which contacts only the fresh feed, i.e., is situated outside the recycle loop. In this embodiment, operating conditions, including temperature and space velocity, are adjusted to convert a major fraction of the ethylbenzene in this reactor. A second reactor in the recycle loop contains the crystalline aluminosilicate catalyst having a crystal size of less than about 1 micron.

Figure 4:
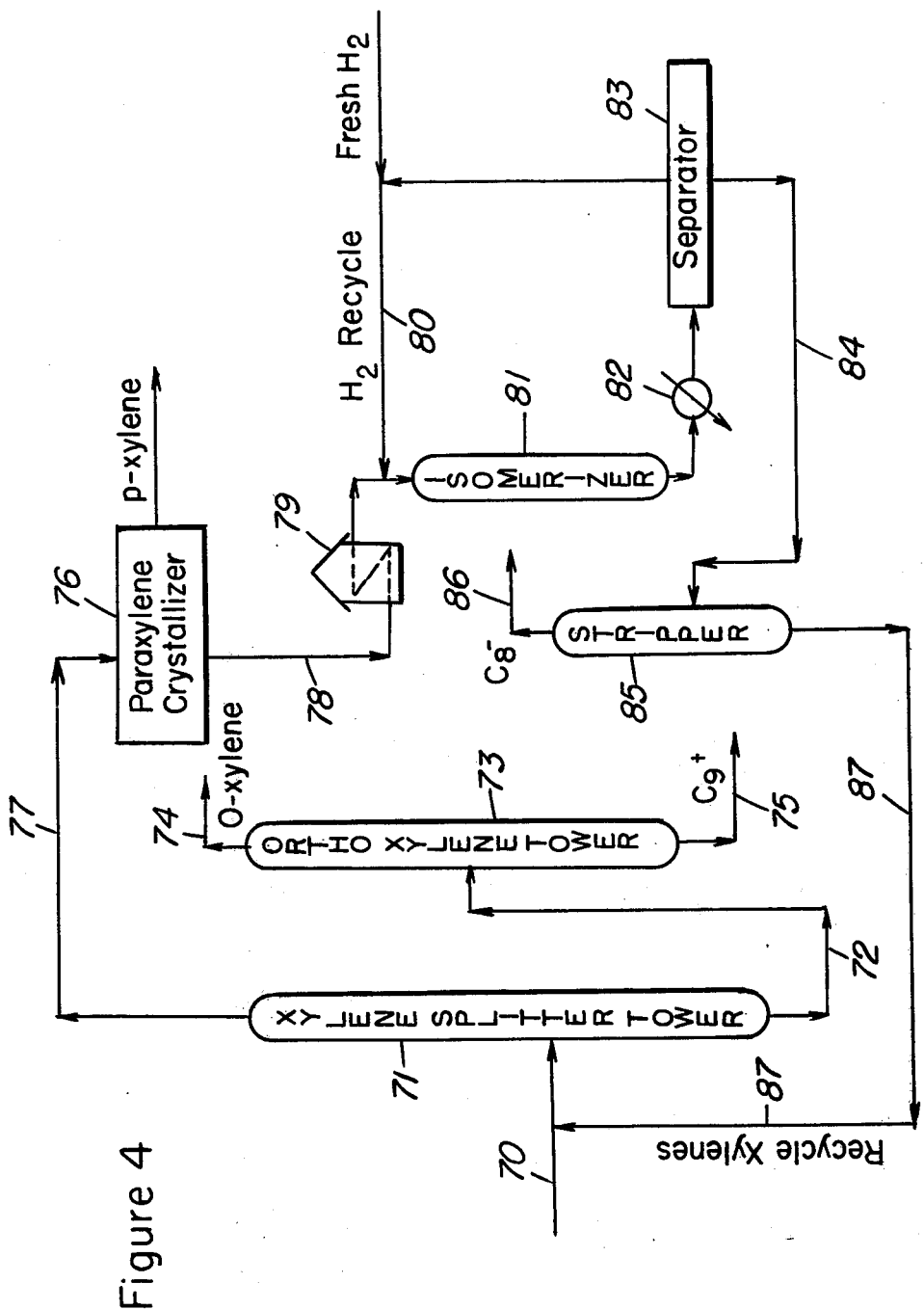
FIG. 4 shows, in schematic fashion, a system utilizing in combination xylene splitter and ortho xylene towers and an isomerization reactor containing crystalline zeolite catalysts of differing crystallite size, which system is particularly applicable when ortho- and para-xylenes are desired products.

In a further embodiment, shown in FIG. 4, the crystalline aluminosilicate catalyst of greater than about 1 micron crystal size is contained in a reactor to which a feed having a depleted ortho and para-xylene content is conducted.

With the aromatic $C_8$ feed mixture utilized herein containing ethylbenzene, and xylene, a certain quantity of ethylbenzene has to undergo conversion in the isomerization reactor to prevent build-up in the recycle system. Inevitably, some of the xylene is simultaneously converted to less valuable products. Utilizing the crystalline aluminosilicate catalyst having a crystal size of at least about 1 micron described hereinabove, it has been found that considerably less xylene is converted for a given amount of ethylbenzene converted, i.e., the selectivity ratio $f_{EB}/f_{XYL}$ is larger, where $f_{EB}$ is the fraction of ethylbenzene in the feed that is converted and $f_{XYL}$ is the fraction of xylene in the feed that is converted.

Turning now to FIG. 1, a $C_8$ aromatics feed containing ethylbenzene, para-xylene, meta-xylene and ortho-xylene is fed through line 10 to crystallizer 11, from which para-xylene is removed. Residual is removed from the crystallizer through line 13 to isomerization reactor 14 containing the above-described crystalline aluminosilicate zeolite catalyst having a crystal size greater than about 1 micron present in major amount and a smaller amount of similar catalyst of less than 1 micron crystal size. The catalysts of varying crystal size may be present as a physical mixture or the catalyst having a crystal size of greater than about 1 micron should be present as a bed at the point of initial contact of the incoming stream. The isomerizate product exits from the reactor through line 15 to stripper 16 where products lighter than $C_8$ are removed as overhead through line 17, $C_8$ and heavier materials pass from stripper 16 through line 18 to splitter tower 19 where $C_9$ and heavier materials are removed through line 20. $C_8$ materials removed from the splitter tower through line 21 are conducted to crystallizer 11 and the cycle repeated.

In the embodiment of FIG. 2, a $C_8$ aromatics feed containing ethylbenzene, para-xylene, meta-xylene and ortho-xylene is fed through line 30 to crystallizer 31, from which para-xylene is removed. Residual is removed from the crystallizer through line 33 to isomerization reactor 34 containing the described crystalline aluminosilicate zeolite catalyst having a crystal size greater than about 1 micron. The isomerizate product exists from reactor 34 through line 35 to a second isomerization reactor 36 containing the crystalline aluminosilicate zeolite catalyst having a crystal size less than about 1 micron. The resulting isomerized product is removed through line 37 to stripper 38 from which products lighter than $C_8$ are removed as overhead through line 39. $C_8$ and heavier materials pass from stripper 38 through line 40 to splitter tower 41 where $C_9$ and heavier materials are removed through line 42. $C_8$ materials removed from the splitter tower through line 43 are conducted to crystallizer 31 and the cycle repeated.

In the embodiment of FIG. 3, a $C_8$ aromatic feed containing ethylbenzene, para-xylene, meta-xylene and ortho-xylene is fed through line 50 to isomerization reactor 51 containing the described crystalline aluminosilicate zeolite catalyst having a crystal size greater than about 1 micron. The isomerizate product passes from reactor 51 through line 52 to stripper 53 from which products lighter than $C_8$ are removed as overhead through line 54. $C_8$ and heavier materials pass from stripper 53 through line 55 to splitter tower 56 from which $C_9$ and heavier materials are removed through line 57. $C_8$ materials removed from the splitter tower through line 58 are conducted to crystallizer 59, from which para-xylene is removed through line 60. Residual is removed from the crystallizer 59 through line 61 to isomerization reactor 62 containing the crystalline aluminosilicate zeolite catalyst having a crystal size less than about 1 micron. The resulting isomerized product is removed through line 63 to stripper 53 and the cycle repeated.

In the embodiment of FIG. 4, a $C_8$ aromatic feed containing ethylbenzene and xylenes is fed through line 70 to xylene splitter tower 71. The bottoms from the xylene splitter constituted by o-xylene and $C_9$ aromatics passes by line 72 to the o-xylene tower 73 from which o-xylene is taken overhead at line 74 and heavy ends are removed by line 75. The overhead from xylene splitter tower 71 is transferred to para-xylene crystallizer 76 through line 77. The crystallizer operates in a manner described in U.S. Pat. No. 3,662,013 to Machell et al.

Since its melting point is much higher than that of the other $C_8$ aromatics, p-xylene is readily separated in the crystallizer after refrigeration of the stream and a xylene mixture lean in p-xylene is transferred to an isomerization unit through line 78. The isomerization charge passes through a heater 79, is admixed with hydrogen admitted through line 80 and the mixture introduced to the reactor 81.

Isomerized product from reactor 81 is cooled in heat exchanger 82 and passed to a high pressure separator 83 from which separated hydrogen can be recycled in the process. The liquid product of the isomerization passes by line 84 to a stripper 85 from which light-ends are passed overhead by line 86. The remaining liquid product constituted by $C_8+$ hydrocarbons is recycled in the system by line 87 to the inlet of xylene stripper column 71.

The following examples are illustrative of the process of the invention.

EXAMPLES 1-3

A feed constituting a blend of ethylbenzene and mixed xylenes, having the composition set forth in Table I below, was passed over a catalyst of HZSM-5 characterized by an average crystal size of about 0.5 micron hereinafter referred to as Catalyst A at a temperature of 650° F., a pressure of 25 psig and weight hourly space velocities of 10, 20 and 40. The product compositions and selectivities obtained in each instance are given in Table I.

In this and other tables, hereinafter set forth:
$\Delta EB$ is the amount of ethylbenzene converted;
EB is the amount of ethylbenzene in the isomerization feed;
$f_{EB} = \Delta EB/EB \times 100$ is the percent of ethylbenzene converted;

ΔXYL is the amount of xylene converted;
XYL is the amount in the isomerization feed;
$f_{XYL} = \Delta XYL/XYL \times 100$ is the percent xylene converted.

TABLE I

| | Feed | Example 1 | Example 2 | Example 3 |
|---|---|---|---|---|
| Temp. (°F.) | | 650 | 650 | 650 |
| WHSV | | 10 | 20 | 40 |
| Product Analysis (wt. %) | | | | |
| $C_5^-$ | | 0.17 | 0.14 | 0.16 |
| Benzene | 0.04 | 3.27 | 2.09 | 1.23 |
| Toluene | 0.07 | 1.06 | 0.51 | 0.29 |
| Ethylbenzene | 19.61 | 13.14 | 15.40 | 17.05 |
| p-xylene | 9.42 | 18.32 | 18.67 | 17.89 |
| m-xylene | 50.38 | 40.89 | 41.77 | 43.07 |
| o-xylene | 20.48 | 17.40 | 18.01 | 18.49 |
| $C_9^+$ | — | 5.74 | 3.41 | 1.92 |
| $f_{EB} = \Delta EB/EB \times 100$ | | 33.0 | 21.5 | 13.1 |
| $f_{XYL} = \Delta XYL/XYL \times 100$ | | 4.57 | 2.27 | 1.03 |
| $f_{EB}/f_{XYL}$ | | 7.2 | 9.5 | 12.7 |

EXAMPLES 4-6

A blend comprising ethylbenzene and mixed xylenes, having the composition shown in Table II below, was passed over a catalyst of HZSM-5 characterized by an average crystal size of about 2 microns, hereinafter referred to as Catalyst B, at 650° F., 25 psig and weight hourly space velocities of 5, 10 and 20. The product compositions and selectivities obtained in each instance are shown in Table II.

TABLE II

| | Feed | Example 4 | Example 5 | Example 6 |
|---|---|---|---|---|
| Temp. (°F.) | | 650 | 650 | 650 |
| WHSV | | 5 | 10 | 20 |
| Product Analysis (wt. %) | | | | |
| $C_5^-$ | | 1.31 | 0.65 | 0.38 |
| Benzene | 0.04 | 3.60 | 2.59 | 1.62 |
| Toluene | 0.11 | 1.51 | 0.86 | 0.35 |
| Ethylbenzene | 18.42 | 10.40 | 12.50 | 14.76 |
| p-xylene | 8.92 | 17.61 | 17.09 | 15.19 |
| m-xylene | 53.14 | 42.74 | 44.56 | 47.07 |
| o-xylene | 19.36 | 17.67 | 18.03 | 18.39 |
| $C_9^+$ | | 4.96 | 3.59 | 2.23 |
| $f_{EB} = \Delta EB/EB \times 100$ | | 43.5 | 32.1 | 19.9 |
| $f_{XYL} = \Delta XYL/XYL \times 100$ | | 4.21 | 2.14 | 0.96 |
| $f_{EB}/f_{XYL}$ | | 10.3 | 15.0 | 20.8 |

EXAMPLES 7-9

A blend comprising ethylbenzene and mixed xylenes, having the composition shown in Table III below, was passed over a catalyst HZSM-5, chemically modified to contain 6 weight percent MgO, hereinafter referred to as Catalyst C, characterized by an average crystal size of about 2 microns at 650° F. 25 psig and weight hourly space velocities of 7.7, 15.4 and 30.8. The product compositions and selectivities obtained in each instance are shown in Table III.

TABLE III

| | Feed | Example 7 | Example 8 | Example 9 |
|---|---|---|---|---|
| Temp. (°F.) | | 650 | 650 | 650 |
| WHSV | | 7.7 | 15.4 | 30.8 |
| Product Analysis (wt. %) | | | | |
| $C_5^-$ | | 0.45 | 0.40 | 0.26 |
| Benzene | 0.04 | 2.91 | 2.50 | 1.37 |
| Toluene | 0.07 | 1.07 | 0.76 | 0.26 |
| Ethylbenzene | 19.70 | 13.33 | 14.18 | 16.41 |
| p-xylene | 9.35 | 11.41 | 10.88 | 10.18 |
| m-xylene | 50.48 | 48.20 | 48.83 | 49.78 |
| o-xylene | 20.36 | 19.39 | 19.57 | 19.94 |
| $C_9^+$ | | 3.09 | 3.74 | 1.65 |
| $f_{EB} = \Delta EB/EB \times 100$ | | 32.3 | 28.0 | 16.6 |
| $f_{XYL} = \Delta XYL/XYL \times 100$ | | 1.48 | 1.13 | 0.26 |
| $f_{EB}/f_{XYL}$ | | 21.8 | 24.8 | 63.8 |

EXAMPLES 10-12

A feed blend comprising ethylbenzene and mixed xylenes, having the composition shown in Table IV below, was passed through a catalyst bed, hereinafter collectively referred to as Catalyst D, the upper ⅔ of which making initial contact with the feed, was HZSM-5 having a crystal size of about 2 microns and the lower ⅓ of which was HZSM-5 having a crystal size of about 0.5 micron. Reaction conditions included a temperature of 650° F., a pressure of 25 psig and weight hourly space velocities of 5, 10 and 20. The product compositions and selectivities obtained in each instance are shown in Table IV.

TABLE IV

| | Feed | Example 10 | Example 11 | Example 12 |
|---|---|---|---|---|
| Temp. (°F.) | | 650 | 650 | 650 |
| WHSV | | 5 | 10 | 20 |
| Product Analysis (wt. %) | | | | |
| $C_5^-$ | | 1.96 | 0.96 | 0.64 |
| Benzene | 0.05 | 3.55 | 2.88 | 1.79 |
| Toluene | 0.20 | 1.41 | 0.87 | 0.40 |
| Ethylbenzene | 19.84 | 12.02 | 13.72 | 15.92 |
| p-xylene | 9.54 | 17.85 | 17.63 | 16.90 |
| m-xylene | 49.50 | 40.50 | 41.82 | 43.13 |
| o-xylene | 20.71 | 17.27 | 18.04 | 18.78 |
| $C_9^+$ | | 5.34 | 4.07 | 2.42 |
| $f_{EB} = \Delta EB/EB \times 100$ | | 39.5 | 30.9 | 19.6 |
| $f_{XYL} = \Delta XYL/XYL \times 100$ | | 5.33 | 2.98 | 1.31 |
| $f_{EB}/f_{XYL}$ | | 7.4 | 10.4 | 14.9 |

Figure 5:
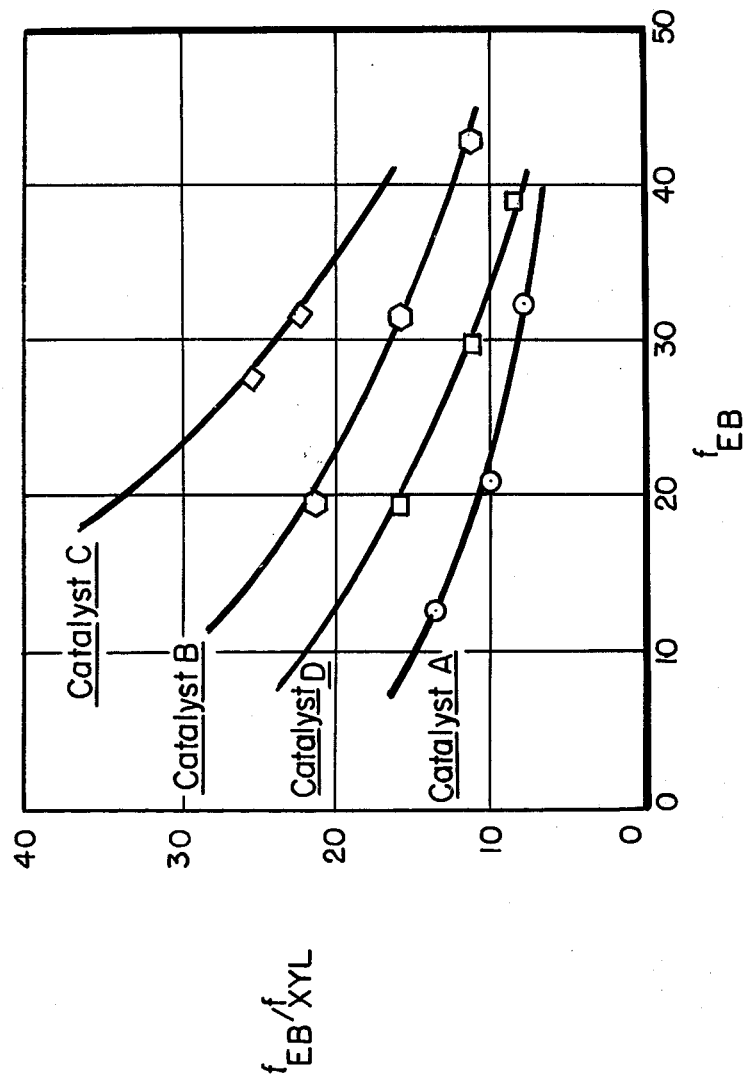
FIG. 5 shows a comparison of xylene selectivities expressed in terms of the ratio of relative ethylbenzene loss to relative xylenes loss ($f_{EB}/f_{XYL}$).

A comparison of the xylene selectivities of the four catalysts utilized in the above examples is shown in FIG. 5. Referring more particularly to this Figure, selectivity is expressed in terms of the ratio of relative ethylbenzene loss to relative xylenes loss ($f_{EB}/f_{XYL}$). It will be evident from the plotted results that there is a marked improvement in selectivity obtained utilizing Catalysts B, C and D over comparable use of the conventional catalyst, exemplified by Catalyst A.

It is to be understood that the foregoing description is merely illustrative of preferred embodiments of the invention of which many variations may be made by those skilled in the art within the scope of the following claims without departing from the spirit thereof.

What is claimed is:

1. A process for isomerizing an isomerization feed containing an aromatic $C_8$ mixture of ethylbenzene and xylene, in which the para-xylene content is less than equilibrium which comprises contacting said feed, under conversion conditions, with a catalyst comprising a crystalline aluminosilicate zeolite having a crystal size of at least about 1 micron, a silica to alumina ratio of at least about 12 and a constraint index within the approximate range of 1 to 12 to yield an isomerization product characterized by a reduced ethylbenzene content and an enhanced para-xylene content.

2. The process of claim 1 wherein said conversion conditions include a temperature of from about 400° to about 1000° F., a pressure of from about 0 to about 1500 psig and a weight hourly space velocity of between about 0.5 and about 100.

3. The process of claim 1 wherein said conversion conditions include a temperature of from about 500° to about 950° F., a pressure of from about 25 to about 1000 psig and a weight hourly space velocity of between about 1 and about 50.

4. The process of claim 1 wherein said aromatic $C_8$ mixture consists essentially of ethylbenzene, para-xylene, meta-xylene and ortho-xylene.

5. The process of claim 1 wherein said isomerization feed contains said aromatic $C_8$ mixture and up to 30 weight percent of non-aromatic hydrocarbons.

6. The process of claim 1 wherein said crystalline aluminosilicate zeolite is ZSM-5.

7. The process of claim 1 wherein said crystalline aluminosilicate zeolite is ZSM-5 predominantly in the hydrogen form.

8. The process of claim 1 wherein the crystal size of said crystalline aluminosilicate zeolite is within the approximate range of 1 to 20 microns.

9. The process of claim 1 wherein the crystal size of said crystalline aluminosilicate zeolite is within the approximate range of 1 to 6 microns.

10. The process of claim 6 wherein the ZSM-5 is present in combination with a binder therefor.

11. The process of claim 1 wherein said crystalline aluminosilicate zeolite is characterized by a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of $4.5 \pm 0.8$ mm. of mercury.

12. The process of claim 1 wherein said crystalline aluminosilicate has combined therewith between about 0.5 and about 40 weight percent of a difficulty reducible oxide.

13. The process of claim 12 wherein said difficulty reducible oxide is magnesium oxide.